United States Patent [19]

Gerstein

[11] 4,033,895
[45] July 5, 1977

[54] NON-IRRITATING SHAMPOO COMPOSITIONS CONTAINING STEARYL AMINE OXIDE

[75] Inventor: Terry Gerstein, Merrick, N.Y.

[73] Assignee: Revlon, Inc., New York, N.Y.

[22] Filed: Dec. 24, 1975

[21] Appl. No.: 644,131

[52] U.S. Cl. .............................. 252/106; 252/547; 252/548; 252/550; 424/70

[51] Int. Cl.$^2$ ................... C11D 1/14; C11D 3/48; C11D 1/84

[58] Field of Search .................. 252/106, 550, 547; 424/245, 289

[56] References Cited

UNITED STATES PATENTS

| | | | |
|---|---|---|---|
| 3,086,943 | 4/1963 | Lang | 252/547 X |
| 3,223,647 | 12/1965 | Drew et al. | 252/547 X |
| 3,236,733 | 2/1966 | Karsten et al. | 252/106 X |
| 3,356,727 | 12/1967 | Koebner et al. | 260/570.7 |
| 3,489,686 | 1/1970 | Parran | 252/106 |
| 3,496,110 | 2/1970 | Shumway et al. | 252/142 |
| 3,549,542 | 12/1970 | Holderby | 252/547 X |
| 3,590,122 | 6/1971 | Roberts et al. | 424/70 |
| 3,785,985 | 1/1974 | Grand | 252/106 |
| 3,808,311 | 4/1974 | Olson et al. | 424/70 |
| 3,926,861 | 12/1975 | Gerecht | 252/542 |

OTHER PUBLICATIONS

Riso, "Protein Derived Detergents," Soap & Chemical Specialties, May 1963, pp. 82–84, 151, 153, 155, 157, 158.

*Primary Examiner*—P.E. Willis, Jr.
*Attorney, Agent, or Firm*—Leon E. Tenenbaum

[57] ABSTRACT

The addition of stearyl dimethyl amine oxide to shampoos containing sodium lauryl-sulfate and zinc pyridinethione reduces considerably the irritant properties of such shampoos.

6 Claims, No Drawings

NON-IRRITATING SHAMPOO COMPOSITIONS CONTAINING STEARYL AMINE OXIDE

The present invention relates to shampoo formulations. It particularly relates to shampoo formulations which have been made substantially non-irritating by the addition thereto of amine oxides.

In preparing a shampoo containing as essential ingredients sodium lauryl sulfate as a surfactant and zinc pyridinethione as an anti-dandruff agent, and, if desired, other ingredients, such as foam boosters, conditioners, opacifiers, additional surfactants, perfumes, suspending agents, colorants and preservatives, it was found that the shampoo was somewhat irritating to the scalp. When stearyl dimethyl amine oxide (hereinafter referred to as SDAO) was used in the shampoo as the conditioner to promote wet combability, it was discovered that the shampoo was rendered considerably less irritating to the scalp.

The use of amine oxides in cosmetic systems is old in the art, having been described in J. Soc. Cosmet. Chem 26, 155–168 (1975), and the surfactant properties of long chain amine oxides have also been recognized (J. Am. Oil Chem. Soc. 51, 461–465 (1974). While the article in the J. Soc. Cosmet. Chem. describes cosmetic systems containing amine oxides, that are non-irritating, an examination of these systems shows that they do not contain any substance which itself is irritating, so that the non-irritating properties of these systems is not in any way due to a counter-irritant property of the amine oxide that may be present.

However, I have discovered that when SDAO is added as the conditioner to my shampoos, the irritant properties of these shampoos were considerably reduced; i.e. the SDAO exerts an anti-irritant effect on the irritant properties of the other ingredients in the shampoo. These unexpected results were not obtained at the cost of reducing the cleansing, conditioning and anti-microbial properties of the shampoo.

These results are unpredictable since a compound which exerts an anti-irritant effect in one composition may not exert it in another composition. The mechanism whereby SDAO exerts this effect is not known, nor is it known against which one or more of the ingredients present in the shampoo the effect is exerted. It is possible that the high concentration of sodium lauryl sulfate in the shampoos of the present invention may be responsible for their irritant properties and that the SDAO may counteract the irritant effect of the sodium lauryl sulfate or the combination of sodium lauryl sulfate and zinc pyridinethione.

While the SDAO appears to counteract the irritant effect of sodium lauryl sulfate or the combination of sodium lauryl sulfate and zinc pyridinethion in the shampoos, SDAO may also have a similar counter-irritant effect upon other lauryl sulfate salts or derivatives thereof, such as, for example, potassium lauryl sulfate, sodium lauryl ether sulfate (3 $C_2H_5O$), diethanolamine lauryl sulfate, and the like, as well as on salts of other alkyl sulfates, other alkyl ether sulfates, alkyl aryl sulfonates, alkyl glyceryl sulfates, alkyl glyceryl ether sulfates, and aryl ether sulfates. Examples of such salts are triethanolamine tridecylbenzene sulfonate, sodium xylene sulfonate, sodium lauryl glyceryl sulfate, potassium myristyl sulfate, sodium lauryl glyceryl ether sulfate, sodium nonylphenyl ether sulfate, potassium dodecyl glyceryl sulfate, and the like.

The shampoo made in accordance with the present invention consists essentially in parts by weight of:

| | | |
|---|---|---|
| Sodium lauryl sulfate | | 4–18 |
| Zinc pyridinethione | | 0.1–4 |
| SDAO | | 0.2–12 |
| Water | qs | 100 |

Preferably, the shampoo contains as essential ingredients from about 7–10 parts of sodium lauryl sulfate, 0.5–2 parts of zinc pyridinethione, 2–8 parts of SDAO, and the remainder as water, parts referring to parts by weight. If desired, colorants, perfumes, additional surfactants, suspending agents, foam boosters or stabilizers, opacifiers, and preservatives may be added. The pH is adjusted, as desired, to a range of about 7.0–9.5, preferably about 7.4–8.5, by the addition of an alkali such as sodium hydroxide or an acid such as hydrochloric acid.

Suitable as additional surfactants are fatty acid amides of diethanolamine such as lauric diethanolamide, myristic diethanolamide, stearic diethanolamide, palmitic diethanolamide, oleic diethanolamide and such other compounds wherein the fatty acid moiety contains from about 10 to 20 carbon atoms. Preferably, a mixture of lauric and myristic diethanolamides in a 7:3 weight ratio is used.

An opacifier to whiten the shampoo is frequently used. Suitable opacifiers are fatty acid amide esters of monoethanolamine such as, for example, stearoyl-amino-ethyl stearate wherein the stearoyl radical is attached to each of the amino and hydroxy groups. Other fatty acid groups, containing from about 10 to 20 carbon atoms, such as lauric, myristic, palmitic, oleic, stearic, linolenic acids and the like may be present in place of stearic acid.

Suitable suspending agents are aluminum silicates such as montmorillonites which have the general formula $Al_2O_3.4SiO_2.4H_2O$.

A shampoo made in accordance with the present invention and comprising additional ingredients may contain in parts by weight:

| | |
|---|---|
| Sodium lauryl sulfate | 4–16 |
| Zinc pyridinethione | 0.1–4 |
| 7:3 Mixture of lauric and myristic diethanolamides | 1–8 |
| Stearoyl-amino-ethyl stearate | 2–4 |
| Montmorillonite | 0.5–6 |
| SDAO | 0.5–12 |
| Water | qs 100 |
| pH | 7.0–9.5 |

The sodium lauryl sulfate is used in an aqueous solution containing about 28% by weight of the sodium lauryl sulfate, and the zinc pyridinethione is used in an aqueous suspension containing about 48% by weight of the zinc pyridinethione SDAO is available in an aqueous containing 25% by weight of SDAO.

The invention will be more fully shown in the examples which follow, but it is to be understood that these examples are for illustration only and are not to be considered as limiting. In these examples all amounts are given parts by weight and a percentage figure in parenthesis following the name of the ingredient indicates the percentage by weight of the ingredient in the composition used.

| Example 1 | |
|---|---|
| Sodium lauryl sulfate (28%) | 25.0 |
| Montmorillonite | 2.0 |
| Zinc pyridinethione (48%) | 2.1 |
| 7:3 Mixture of lauric and myristic diethanolamides | 6.0 |
| Stearoyl-aminoethyl stearate | 3.0 |
| SDAO (25%) | 8.0 |
| Water | qs 100 |
| Example 2 | |
| Butoxypoloxyethylene glycol | 0.7 |
| Montmorllonite | 2.0 |
| Sodium lauryl sulfate (28%) | 35.0 |
| 7:3 mixture of lauric and myristic diethanolamides | 6.0 |
| Protein hydrolysate | 0.2 |
| Stearoyl-amino-ethyl stearate | 3.0 |
| SDAO (25%) | 8.0 |
| Zinc pyridinethione (48%) | 2.1 |
| Perfume oil | 0.2 |
| Concentrated hydrochloric acid was added to adjust the pH to about 8.0, and water qs 100. | |
| Example 3 | |
| Sodium lauryl sulfate (28%) | 36.0 |
| Montmorillonite | 2.0 |
| Zinc pyridinethione (48%) | 2.0 |
| SDAO (25%) | 32.00 |
| Water | qs 100 |
| Example 4 | |
| Sodium lauryl sulfate (28%) | 14.5 |
| Zinc pyridinethione (48%) | 1.0 |
| SDAO (25%) | 2.0 |
| Water | qs 100 |
| Example 5 | |
| Sodium lauryl sulfate (28%) | 30.0 |
| Zinc pyridinethione (48%) | 1.0 |
| SDAO (25%) | 3.0 |
| Water | qs 100 |
| Example 6 | |
| Sodium lauryl sulfate (28%) | 25.0 |
| Zinc pyridinethione (48%) | 2.1 |
| Montmorillonite | 3.0 |
| Perfume oil | 1.0 |
| 7:3 Mixture of lauric acid and myristic diethanolamides | 2.0 |
| SDAO (25%) | 32.0 |
| Water | qs 100 |
| Example 7 | |
| Sodium lauryl sulfate (28%) | 32.0 |
| 7:3 Mixture of lauric and myristic diethanolamides | 3.0 |
| Montmorillonite | 2.0 |
| Perfume Oil | 1.0 |
| Protein hydrolysate | 0.5 |
| Zinc pyridinethione (48%) | 1.9 |
| SDAO (25%) | 30.0 |
| Water | qs 100 |

I claim:

1. An aqueous non-irritating shampoo consisting essentially in parts by weight of

| sodium lauryl sulfate | 4–18 |
|---|---|
| zinc pyridinethione | 0.1–4 |
| stearyl dimethyl amine oxide | 0.2–12 |
| water q.s. | 100 |

2. An aqueous non-irritating shampoo according to claim 1 which contains in parts by weight

| sodium lauryl sulfate | 7–10 |
|---|---|
| zinc pyridinethione | 0.5–2 |
| stearyl dimethyl amine oxide | 2–8 |

3. An aqueous non-irritating shampoo according to claim 2 which contains in parts by weight

| sodium lauryl sulfate | 9.8 |
|---|---|
| zinc pyridinethione | 1 |
| stearyl dimethyl amine oxide | 2 |

4. An aqueous non-irritating shampoo according to claim 1 having a pH from about 7.0 – 9.5.

5. An aqueous non-irritating shampoo according to claim 4, having a pH from about 7.4 – 8.5.

6. An aqueous non-irritating shampoo according to claim 3 containing in parts by weight

| Butoxypolyoxyethylene glycol | 0.7 |
|---|---|
| Montmorillonite | 2.0 |
| Sodium lauryl sulfate | 9.8 |
| 7:3 Mixture of lauric and myristic diethanolamides | 6.0 |
| Protein hydrolysate | 0.2 |
| Stearoyl-amino ethyl stearate | 3.0 |
| Stearyl dimethyl amine oxide | 2.0 |
| Zinc pyridinethione | 1 |
| Perfume oil | 0.2 |
| Water | qs 100 |
| said shampoo having a pH of about 8.0. | |

* * * * *